United States Patent [19]

Shaulov

[11] Patent Number: 4,870,867
[45] Date of Patent: Oct. 3, 1989

[54] CROSSED LINEAR ARRAYS FOR ULTRASONIC MEDICAL IMAGING

[75] Inventor: Avner Shaulov, Monsey, N.Y.

[73] Assignee: North American Philips Corp., New York, N.Y.

[21] Appl. No.: 290,472

[22] Filed: Dec. 27, 1988

[51] Int. Cl.⁴ .............................................. G01N 29/00
[52] U.S. Cl. .................................. 73/625; 128/662.05; 310/334
[58] Field of Search ................. 73/606, 628, 624, 625, 73/626; 310/334, 335; 128/662.05, 662.03, 661.01

[56] References Cited

U.S. PATENT DOCUMENTS

| | | | |
|---|---|---|---|
| 3,881,164 | 4/1975 | Kossoff | 128/661.01 |
| 4,570,488 | 2/1986 | Miwa et al. | 73/626 |
| 4,580,451 | 4/1986 | Miwa et al. | 128/661.01 |
| 4,640,291 | 2/1987 | 't Hoen | 310/335 |
| 4,671,293 | 6/1987 | Shaulov | 128/660 |

FOREIGN PATENT DOCUMENTS 57-113700  7/1982  Japan .................................. 310/334

OTHER PUBLICATIONS

"Hybrid Linear and Matrix Acoustic Arrays", by M. Pappalardo, Ultrasonics, Mar. 1981 (310/334).

Primary Examiner—John Chapman
Assistant Examiner—Louis M. Arana
Attorney, Agent, or Firm—William L. Botjer

[57] ABSTRACT

An improved piezoelectric transducer permitting linear scanning along two intersecting planes. The transducer is fabricated from a cross shaped piezoelectric plate covered on both faces with metallic electrodes. First and second linear arrays are formed by the partial dicing of the opposite faces of the electrodes and plate. The two segments of the orthogonal arrays are integrated in the crossed area. An aperture may be disposed in the central area so as to permit a surgical implement, such as a biopsy needle, to be inserted into the tissue under ultrasonic visualization. Scanning electronics are alternately connectable to each of the arrays by means of a multiple pole switch under the control of a clock.

13 Claims, 2 Drawing Sheets

CROSSED LINEAR ARRAYS FOR ULTRASONIC MEDICAL IMAGING

BACKGROUND OF INVENTION

This invention relates to ultrasonic transducers and more particularly to an ultrasonic transducer in the form of a crossed linear array for ultrasonic medical imaging and for biopsy needle guidance.

In a linear array ultrasonic scanner the transducer consists of a series of individually addressable piezoelectric segments which emit ultrasonic waves when energized by the application of electricity. In a linear array the individual segments of the transducer are activated sequentially from one end to the other to generate a rectangular image. The ultrasonic waves emitted by the transducer are focused by the activating electronics and by an acoustic lens disposed between the transducer and the tissue to be imaged. The ultrasonic image generated by a linear array transducer is that of a rectangular "slice" of the tissue.

However, the ultrasonic image generated is only two dimensional. That is, the image has no usable thickness information. Accordingly, the use of a linear array scan to place, for example, a biopsy needle is at best difficult because of the lack of usable thickness information. If the needle is not precisely in the plane of scan the needle will be invisible to the physician. Furthermore, under certain circumstances even if the needle is visible it may still be improperly placed. Accordingly, it is desirable that a physician be able to determine in three dimensions where a biopsy needle has been placed.

In ultrasonic medical imaging another common type of scanning mode used with a segmented transducer is the so called "phased array" system. In a phased array the activating electronics are used to simulate the scanned motion of a transducer without actually physically moving the transducer. In a phased array system the segments of the transducer are activated such that the segments of certain sections of the transducer are delayed with respect to the others. Such a device produces a wedge shaped "sector scan" image. However in the sector scan the image formed is again only two dimensional with no useful thickness information.

A transducer of the phased array typed suitable for ultrasonic imaging in more than one plane is shown in U.S. Pat. No. 4,671,293 which issued to the inventor herein and shows a phased array two plane transducer. However, the electronics needed to drive a phased array transducer are considerably more complex than that of a linear array. Accordingly, an improved two plane linear array device suitable for imaging in two planes to permit accurate biopsy needle placement is desired. The present invention is directed to providing such a device.

U.S. Pat. No. 4,570,488 is directed to a various two dimensional arrangement of ultrasonic linear arrays. In one embodiment, two perpendicular linear arrays overlap each other. In another example, two perpendicular linear arrays are arranged across each other. However at the intersection of the linear arrays the elements of the transducer are divided into a large number of small elements which form a two dimensional array. Such an array is disadvantageous because a large number of electrical connections to the individual elements of the two dimensional array are required at the crossing area. Furthermore, the electronics required to drive the array at the center so as to provide two orthogonal linear scans are also quite complex.

SUMMARY OF THE INVENTION

The present invention is directed to providing a relatively simple and inexpensive piezoelectric transducer that includes two intersecting linear arrays without forming a two dimensional array in the intersection area. This is accomplished by exploiting the two opposite faces (front and back) of a piezoelectric plate to form the two intersecting arrays. Furthermore, the crossed linear array may include a guide hole in the center through which a biopsy needle may be inserted under ultrasonic visualization.

The transducer constructed in accordance with the present invention is fabricated from a cross shaped piezoelectric plate covered on both faces with thin metallic electrodes. First and second linear arrays are formed by partially dicing the opposite faces the plate. In this configuration the two segments of the orthogonal arrays are integrated in the crossed area. Uniformity of the array elements can be assured by using a composite piezoelectric material or by cross dicing the entire area of the plate. For biopsy applications a guiding hole for the needle is disposed at the center of the crossed arrays.

BRIEF DESCRIPTION OF THE DRAWINGS

For better understanding of the invention reference is made to the following drawings which are to be taken in connection with the detailed specification to follow, in which.

DETAILED DESCRIPTION OF THE PREFERRED EMBODIMENTS

Figure 1:
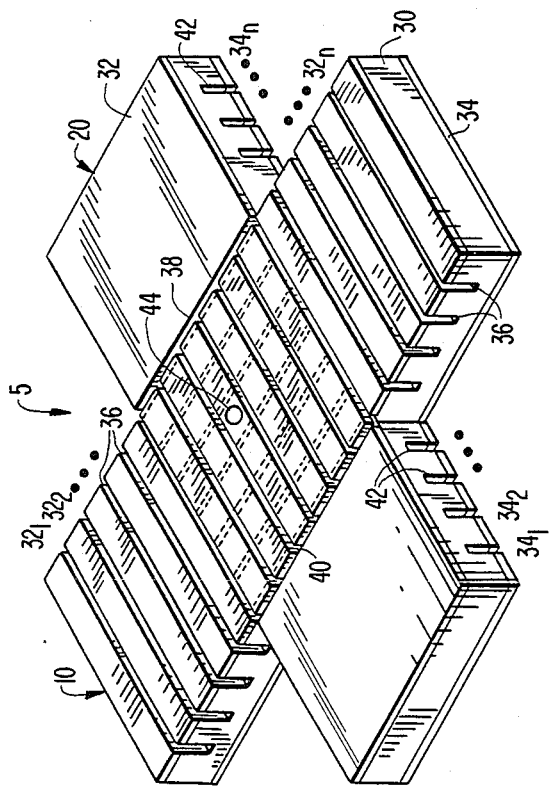
FIG. 1 is a perspective view of the crossed linear arrays forming a transducer constructed in accordance with the present invention.

FIG. 1 illustrates a transducer constructed in accordance with the present invention. Transducer 5 is cross shaped in plan view and comprises a first linear array 10 and second linear array 20 disposed orthogonally to each other each array extending along an "arm" of transducer 5. Transducer 5 consists of a plate 30 of piezoelectric material. Disposed on the upper face of plate 30 is conductive electrode 32 and on the lower face of the plate 30 is a conductive electrode 34. The electrical connection to activate piezoelectric plate 30 is by means of electrodes 32, 34 which are in turn connected to the activating and scanning circuitry discussed below. The piezoelectric material of plate 30 is preferably a composite constructed from a matrix of parallel rods of a piezoelectric ceramic material distributed in an electrically insulating binding material such that each of the rods is completely surrounded by the insulating and damping material. The rods extend from the upper surface of plate 30 to the lower surface of plate 30 and are in electrical contact with the respective electrodes 32, 34. Alternatively, any piezoelectric material suitable for ultrasonic imaging applications is also usable in connection with this device. Plate 30 may either be formed as cross shaped or the appropriate shape may be cut from a rectangular or square blank. Furthermore, arrays 10, 20 need not intersect at 90° as other crossing angles may also be constructed.

Array 10 is defined by a series of traverse grooves 36 cut into electrode 32 and the upper surface of plate 30 which do not extend to its lower surface. Grooves 36 divide electrode 32 into a series of independently addressable electrodes $32_1, 32_2, \ldots 32_n$. Grooves 36 serve to electrically isolate the segments of array 10 for independent addressing by the scanning electronics. The lower electrode 34 remains uncut along array 10, except at its center section, and serves as its ground. The center section of lower electrode 34 is cut only for the grooves defining array 20. Grooves 38, 40 are disposed along the central section of array 10 in line with its edges to isolate its segments from those of array 20.

Linear array 20 is defined by a series of transverse grooves 42 cut into electrode 34 and the lower surface of plate 30 which do not extend to the upper surface of plate 30. Thus, electrode 34 is divided into a series of independently addressable electrodes $34_1, 34_2, \ldots 34_n$ along the lower surface of array 20 and they and plate 30 form an independent linear array which is orthogonally disposed with respect to array 10. In linear array 20 electrode 32 on the upper surface of plate 30 serves as the ground electrode. Disposed at the center of arrays 10 and 20 is an aperture 44 which extends completely through plate 30 and electrodes 32, 34. Aperture 44 permits the insertion of a biopsy needle so it can be guided by ultrasonic visualization in two orthogonal planes.

To accomplish the out of plane focusing for the two arrays (10, 20), a spherical lens is attached to the intersection area and conventional cylindrical acoustic lenses, of the same radius of curvature, are attached to the portions of the arrays out of the intersection area. The spherical lens acts as a combination of two orthogonal cylindrical lenses. For each array, one of these lenses performs the out of plane focusing, while the other introduces a phase aberration in the lateral direction. This aberration can be compensated electronically by adjusting the delay times for the electronic focusing in the scanning plane.

The crossed linear arrays can be operated sequentially to scan the ultrasonic beam in two orthogonal planes in the following way. A scan along array 10 is obtained by connecting the set of electrodes 32 to the scanning circuit and electrodes 34 to ground. In a similar manner, a scan along array 20 is obtained by connecting the set of electrodes 34 to the scanning circuit and electrode 32 to ground.

Figure 2:
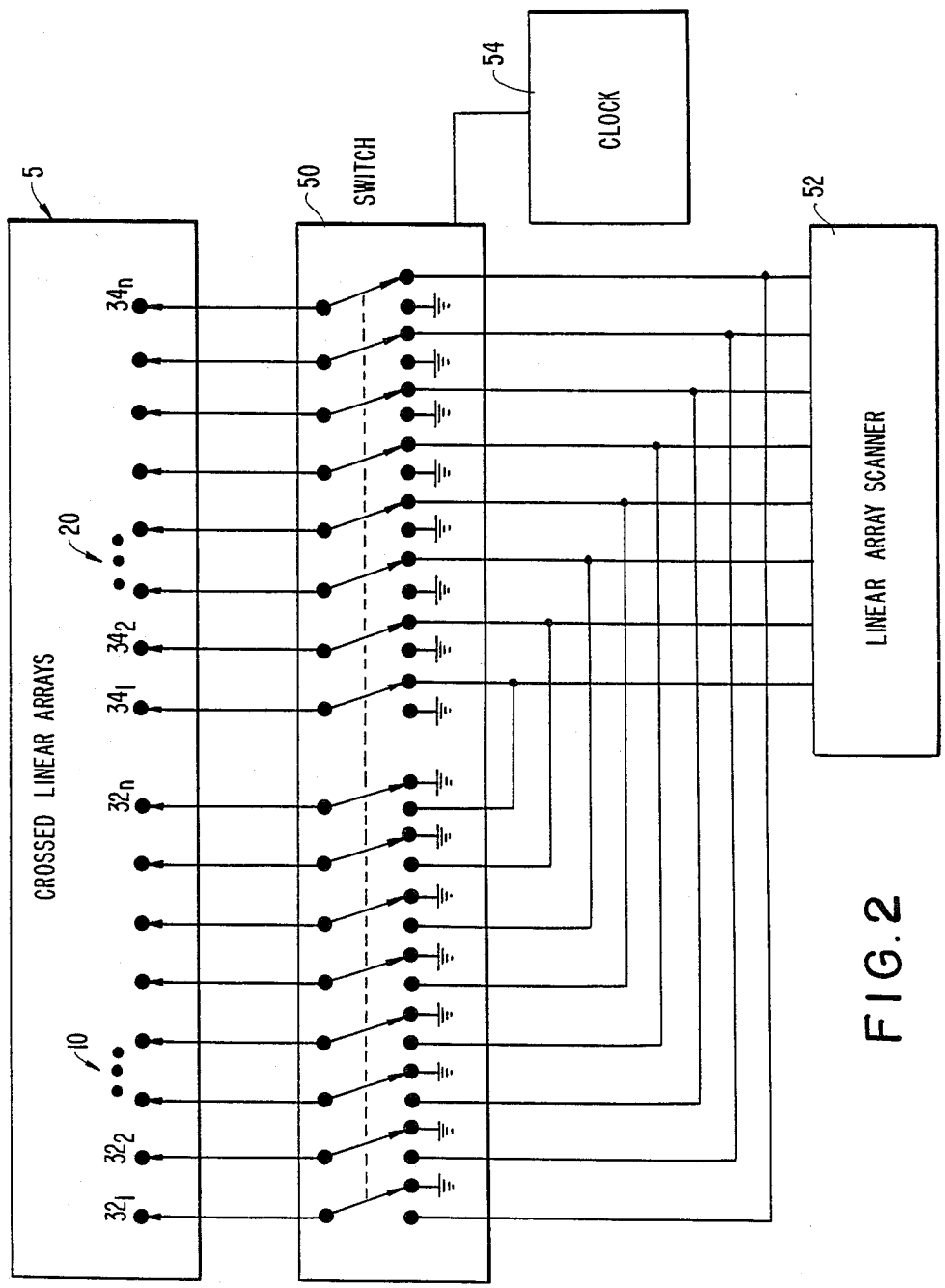
FIG. 2 is a schematic diagram of the switching mechanism for connecting the crossed linear arrays to linear scanning circuitry.

Integration of the crossed linear arrays into a linear array system can be accomplished by means of a switch 50, as shown in FIG. 2. Switch 50 is disposed between transducer 5 and scanning electronics 52 and is controlled by a clock 54. Switch 50 is comprised of a multiple pole switch which switches electrodes 32 of array 10 and electrodes 34 of array 20 for alternate connection to scanning electronics 52. As shown, the electrodes of each array is either switched to scanner electronics 52 or to ground. As shown in FIG. 2 electrodes $34_1, 34_2, \ldots 34_n$ of array 20 are connected to the scanner electronics 52 with electrodes $32_1, 32_2, \ldots 32_n$ of array 10 shorted to ground. Switch 50 swings between the two positions in synchrony with the scanner frame rate under the control of clock 54. In the position shown, array 20 is connected to scanning electronics 52 to provide one field of view and the electrodes of array 10 are connected to ground. Subsequent switching to the other position activates array 10 to provide the orthogonal field of view. Higher data rates, and hence increased frame rates, can be achieved by incorporating parallel processing techniques into the linear array system.

Although the present invention has been described in conjunction with preferred embodiments, it is to be understood that modifications and variations may be resorted to without departing from the spirit of the invention as those skilled in the art will readily understand. Such modifications and variations are considered to be within the purview and scope of the invention and the appended claims to follow.

What is claimed:

1. An ultrasonic transducer comprising:
   a cross shaped plate of piezoelectric material defining first and second arms, and having upper and lower surfaces;
   first and second conductive electrodes disposed on said upper and lower surfaces of said plate;
   a first series of transverse grooves extending along said first arm of said plate, said first series of grooves extending through said first electrode and at least partially through said piezoelectric material;
   a second series of transverse grooves extending along said second arm of said plate, said second series of grooves extending through said second electrode and at least partially through said piezoelectric material; and
   said grooves in said first and second electrodes defining first and second independently addressable arrays of piezoelectric transducers.

2. The ultrasonic transducer as claimed in claim 1 further including linear scanning means connectible to at least one of said first and second arrays.

3. The ultrasonic transducer as claimed in claim 2 further including switch means disposed between said scanner means and said first and second arrays, said switch means alternately switching one of said arrays to said scanning means.

4. The ultrasonic transducer as claimed in claim 3 further including clock means connected to said switch means to synchronously switch said switch means between a first position connected to said first array and a second position connected to said second array.

5. The ultrasonic transducer arrangement as claimed in claim 4 wherein said clock means switch said switch means synchronously with the frame rate of said scanning means.

6. The ultrasonic transducer arrangement as claimed in claim 1 further including an aperture disposed at the center of said first and second arrays, said aperture being sized so as to permit the insertion of a surgical implement through said aperture and into the tissue to be visualized.

7. The transducer arrangement as claimed in claim 1 wherein said first and said second arrays are disposed orthogonally to each other.

8. Ultrasonic imaging equipment comprising:
   a cross shaped plate of piezoelectric material defining first and second arms, and having upper and lower surfaces;
   first and second conductive electrodes disposed on said upper and lower surfaces of said plate;
   a first series of transverse grooves extending along said first arm of said plate, said first series of grooves extending through said first electrode and at least partially through said piezoelectric material;

a second series of transverse grooves extending along said second arm of said plate, said second series of grooves extending through second electrode and at least partially through said piezoelectric material;

said grooves in said first and second electrodes defining first and second independently addressable arrays of piezoelectric transducers;

linear scanning circuitry alternatively connectable to said first and second independently addressable arrays.

9. The ultrasonic transducer as claimed in claim 8 further including switch means disposed between said scanner circuitry and said first and second arrays, said switch means alternately switching one of said arrays to said scanning means.

10. The ultrasonic transducer as claimed in claim 9 further including clock means connected to said switch means to synchronously switch said switch means between a first position connected to said first array and a second position connected to said second array.

11. The ultrasonic transducer arrangement as claimed in claim 10 wherein said clock means switch said switch means synchronously with the frame rate of said scanning circuitry.

12. The ultrasonic transducer arrangement as claimed in claim 8 further including an aperture disposed at the center of said first and second arrays, said aperture being sized so as to permit the insertion of a surgical implement through said aperture and into the tissue to be visualized.

13. The transducer arrangement as claimed in claim 8 wherein said first and said second arrays are disposed orthogonally to each other.

* * * * *